United States Patent [19]

Fontanille et al.

[11] Patent Number: 4,782,118

[45] Date of Patent: Nov. 1, 1988

[54] CEMENT FOR FIXING A BONE PROSTHESIS

[75] Inventors: Michel Fontanille, Bordeaux; Myrna Timar, Saint Denis, both of France

[73] Assignee: Ceraver, S.A., Paris, France

[21] Appl. No.: 876,675

[22] Filed: Jun. 20, 1986

[30] Foreign Application Priority Data

Jun. 20, 1985 [FR] France .................. 85 09397

[51] Int. Cl.$^4$ .......................................... C03F 269/00
[52] U.S. Cl. .................... 525/286; 525/260; 525/263; 525/293; 525/301
[58] Field of Search ............... 525/286, 293, 301, 260, 525/263

[56] References Cited

U.S. PATENT DOCUMENTS 3,810,859  5/1974  Milkofalvy ............... 525/286
4,228,062 10/1980  Lee, Jr. et al. ........... 525/286

Primary Examiner—Jacob Ziegler
Attorney, Agent, or Firm—Kenyon & Kenyon

[57] ABSTRACT

A cement for fixing a bone prosthesis, the cement containing:

(a) a solid phase comprising firstly polymethylmethacrylate and a copolymer of methyl methacrylate with an acrylate or a methacrylate of another alcohol, both in powder form, and secondly an organic peroxide suitable for generating free radicals; and (b) a liquid phase comprising methyl methacrylate and an accelerator for accelerating decomposition of the organic peroxide.

The copolymer is an oligomer, and the liquid phase includes as the accelerator for accelerating decomposition of said organic peroxide an acrylate or a methacrylate carrying a tertiary amine function, and as a cross-linking agent a compound having at least two functions in its molecule suitable for reacting with the reactive functions carried by the polymers of the solid phase, or else a double bond and a function suitable for reacting with the reactive functions carried by the polymers of the solid phase.

4 Claims, No Drawings

CEMENT FOR FIXING A BONE PROSTHESIS

The present invention relates to a cement for fixing a bone prosthesis, and in particular an endoprosthesis for a joint, the cement containing:

(a) a solid phase comprising firstly polymethylmethacrylate and a copolymer of methyl methacrylate with an acrylate or a methacrylate of another alcohol, both in powder form, and secondly an organic peroxide suitable for generating free radicals; and (b) a liquid phase comprising methyl methacrylate and an accelerator for accelerating decomposition of the organic peroxide.

Cements of this type have already been described in document GB-A-No. 1130653. Unfortunately, the polymerization reaction of such cements is highly exothermal, such that their temperature rises to about 90° C. while setting after being put into place in a bone. Such a high temperature damages the surrounding bone tissue and this has a deleterious effect on the stability of the prosthesis being fitted. In addition, the accelerator for accelerating decomposition of the organic peroxide is a tertiary amine or an aromatic sulfinic acid, both of which are particularly toxic to the organism.

Preferred implementations of the present invention provide a cement for fixing a bone prosthesis in which the polymerization reaction is less highly exothermic such that its temperature remains below 56° C. during setting, i.e. below the temperature at which protein coagulates, and having an accelerator for accelerating decomposition of the organic peroxide which cannot migrate into the organism after the cement is fully cured, and which therefore does not have a serious toxic effect, even in the long term.

The cement according to the present invention is characterized in that in said solid phase the copolymer is an oligomer, and said alcohol is an aliphatic alcohol carrying a reactive function suitable for subsequent reaction with a molecule in said liquid phase; in addition, said liquid phase includes as the accelerator for accelerating decomposition of said organic peroxide an acrylate or a methacrylate carrying a tertiary amine function enabling the cement to set in bulk in a few minutes, and as a slow and non-exothermal cross-linking agent a compound having at least two functions in its molecule suitable for reacting with said reactive function of said alcohol, or else a compound including a double bond in its molecule and a function suitable for reacting with said reactive function of said alcohol, in such a manner as to generate a multifunctional polymer acting as a cross-linking agent.

The cement preferably incorporates at least one of the following characteristics:

said oligomer is an oligomer of methyl methacrylate with a methacrylate carrying an oxirane function, for example an oligomer of methyl methacrylate with glycidyl methacrylate;

said accelerator for accelerating decomposition of said organic peroxide enabling the cement to set in its bulk in a few minutes is methylanilylglycidyl methacrylate; and it contains about three parts solid phase to one part liquid phase.

A formulation of a cement in accordance with the invention is described below, by way of example.

Its solid phase has the following composition:

| | |
|---|---|
| Polymethylmethacrylate powder | 24 grams |
| Powder of the copolymer of methyl methacrylate with glycidyl methacrylate (an oligomer having a number average molar mass of 1000 to 5000 g/mole) | 12 g |
| Benzoyl peroxide | 0.3 g |
| | 36.3 g |
| Its liquid phase has the following composition: | |
| Methyl methacrylate | 10.9 g |
| Methacrylic acid | 1.03 g |
| Methylanilylglycidyl methacrylate | 0.8 g |
| | 12.73 g |

The solid phase to liquid phase mass ratio is about 3.

The mass z of methacrylic acid is determined using the following general relationship:

$$z = m \cdot \frac{\overline{f}}{\overline{Mn}} \cdot \frac{M'}{f'}$$

Where:

m is the mass of the copolymer (in this case the copolymer of methyl methacrylate with glycidyl methacrylate);

$\overline{f}$ is the average functionality of the copolymer;

$\overline{Mn}$ is the average numeric molar mass of the copolymer;

M' is the molar mass of the reactive molecule inserted in the liquid phase (in this case methacrylic acid), i.e. 86 g/mole, and f' is the functionality of said reactive molecule (i.e. in this case f'=1).

The masses of benzoyl peroxide and methylanilylglycidyl methacrylate are adjusted so as to obtain the desired bulk setting time, given that the polymerization time is about 12 minutes.

Fillers may be added to the solid phase, for example an X-ray opacifier (in particular zirconium dioxide), and stabilizers and other monomers (such as butyl or isobutyl methacrylates) may be added to the liquid phase.

Bulk setting of the cement takes place in two successive stages which correspond to two different reactions taking place after the solid and liquid phases have been mixed together. Before bulk setting takes place, the viscosity of the mixture is no higher than that of a conventional cement, in spite of the high proportion of solid phase.

The first stage is rapid and ensures immediate bulk setting and secures the prosthesis; the second stage is slower and its purpose is to consolidate the cement.

(1) Radical polymerization stage

Bulk setting is initially provided by radical polymerization of the acrylic monomers which are present: methyl methacrylate; methacrylate acid; and methylanilylglycidyl methacrylate.

The free radicals which trigger this polymerization are created by the methylanilylglycidyl methacrylate reacting with the benzoyl peroxide. These free radicals then slowly set off radical polymerization of the methyl methacrylate and of the methacrylic acid, however they also incorporate molecules containing double bonds, namely methylanilylglycidyl methacrylate molecules, into the macromolecular chains being formed. This thus acts simultaneously as a monomer and as an accelerator for accelerating decomposition of the primer.

Polymer chain propagation is then accelerated by partial dissolution of the polymethylmethacrylate powder and of the methyl methacrylate with glycidyl methacrylate copolymer powder.

This setting acceleration effect by increasing viscosity (gel effect) has already been described with prior cements. Polymerization takes place at ever increasing rate and, since the opening of double bonds is an exothermal reaction, a considerable amount of heat is evolved.

In known cements, a portion of the evolved heat is absorbed by the polymethylmethacrylate powder. In addition to this powder, the new cement contains a very large quantity of copolymer which also absorbs a portion of the heat evolved. The low molar mass of the oligomers (methyl methacrylate and glycidyl methacrylate) makes it possible to reduce the proportion of liquid methyl methacrylate without modifying the viscosity and thus to proportionately reduce the amount of heat which is evolved.

Calorimetric tests have been performed under the same conditions both on mixtures of the type described above and on mixtures containing dimethyl-para-toluidine instead of methylanilylglycidyl methacrylate as the polymerization catalyst and without any copolymer of methyl methacrylate with glycidyl methacrylate, and these tests show that the first cements have a maximum temperature of 55° C., whereas the second cements have a maximum temperature in the range 80° C. to 90° C. 55° C. is below the temperature at which proteins coagulate (56° C.), and is therefore much less likely to damage bone tissue in the vicinity of the zone which comes into contact with the cement.

In addition, replacing a relatively toxic tertiary amine such as dimethyl-para-toluidine with a compound which performs the same accelerator function but which also copolymerizes with the main monomer very greatly reduces the long term toxicity due to said molecule.

(2) Formation of a three-dimensional polymeric network:

After radical polymerization has taken place, the cement has set, but it contains chains carrying reactive functions which will give rise to the formation of a three-dimensional network. The rate at which such a network is formed is slow relative to the rate at which radical polymerization takes place: it takes about a week for the structure to stabilize.

The cement medium then contains:

Firstly chains formed by radical polymerization during the first stage and including a few carboxylic functions randomly distributed along the chains, which can be shown diagrammatically by:

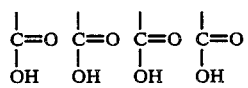

The structural units of these chains are mostly methyl methacrylate units and a few methylanilylglycidyl methacrylate units, together with a few methacrylic acid units.

Secondly there are oligomeric chains of a random copolymer of methyl methacrylate with glycidyl methacrylate as provided in the solid phase. These may be shown diagrammatically as follows:

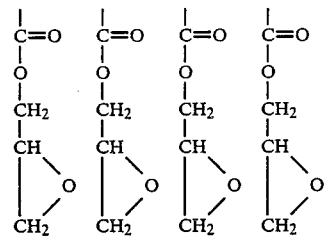

The acidic functions and the oxirane functions react within the bulk of the cement to open the oxirane cycles and form hydroxyls. This causes two independent chains to interconnect via a covalent bond. After about one week, the development of such networks within the bulk of the cement constitutes a thoroughly cross-linked mesh which consolidates the cement and prevents creep. In the end, the cement comprises networks which are semi interpenetrated by linear chains of polymethylmethacrylate.

The cement formed in this way has mechanical properties which are as good as those of known cements, and it is as easy to mix even though it has a higher proportion of solid phase.

However, it no longer rises to too high a temperature when setting, and it avoids the toxicity due to the accelerator for accelerating decomposition of the organic peroxide.

In order to place cement in accordance with the invention in a prosthesis, the liquid and solid phases are mixed, e.g. for 2 to 3 minutes and the mixture is then allowed to stand for 5 to 6 minutes before being inserted into the bone after about 7 to 8 minutes, either by hand or else by means of a syringe.

Although the above-described cement composition appears to be the preferred formulation for performing the present invention, various items may be replaced by others which perform an equivalent function, and the proportions may be modified within limits depending on the time during which it is desirable for the cement to remain malleable, and this applies particularly to the proportions of peroxide and of methylanilylglycidyl methacrylate. Other reactive molecule/oligomer pairs may be used, for example:

| OLIGOMERS IN THE SOLID PHASE | REACTIVE MOLECULES IN THE LIQUID PHASE |
|---|---|
| Copolymers of methyl methacrylate with methacrylic acid | (a) a multiepoxy (f' ≧ 2), e.g. bisphenol A diglycidyl-ether, or (b) a methacrylate or an acrylate including an oxirane function (glycidyl methacrylate) |
| Copolymers of methyl methacrylate with an acrylate or a methacrylate including a secondary amine function | as above |
| Copolymers of methyl methacrylate with glycidyl methacrylate | (a) a multiacid soluble in the liquid phase (f' ≧ 2) (b) a methacrylate or an acrylate including a carboxylic acid function (methacrylic acid or acrylic acid) or a secondary amine function (c) a primary or secondary multiamine soluble in the liquid phase and not inhibiting the first stage of |

| OLIGOMERS IN THE SOLID PHASE | REACTIVE MOLECULES IN THE LIQUID PHASE |
|---|---|
| | radical polymerization. |

The density of the network may be varied by modifying the concentration of glycidyl methacrylate in the copolymer of methyl methacrylate with glycidyl methacrylate.

The flexibility of the copolymer chains may be modified by adding a third monomeric unit for lowering the glass transition temperature, for example an ethyl, butyl or ethyl-2-hexyl acrylate, an n-butyl, isobutyl or glycidyl methacrylate, acrylic acid, methacrylic acid, or bisphenol A diglycidyl-ether.

What is claimed is:

1. A cement for fixing a bone prosthesis, in particular an endoprosthesis for a joint, to a bone, the cement comprising:
   (a) a solid phase, in powder form, including
      a first part consisting of polymethylmethacrylate and an oligomer of methyl methacrylate with glycidyl methacrylate, the glycidyl methacrylate having an oxirane function, and
      a second part consisting of an organic peroxide capable of generating free radicals; and
   (b) a liquid phase including
      methyl methacrylate;
      an accelerator for accelerating decomposition of the organic peroxide, the accelerator including a methacrylate or an acrylate having a tertiary amine function for enabling the cement to set in bulk in a few minutes; and
      a compound consisting of a methacrylate having a carboxylic acid function capable of reacting with the oxirane function of the oligomer.

2. A cement according to claim 1 wherein said accelerator is methylanilylglycidyl methacrylate.

3. A cement according to claim 1 or 2 wherein the weight ratio of said solid phase to said liquid phase is approximately 3 to 1.

4. A cement according to claim 1 wherein the methacrylate having a carboxylic acid function is methacrylic acid.

* * * * *